US00RE45904E

(19) United States
(12) Reissued Patent
Rudman

(10) Patent Number: US RE45,904 E
(45) Date of Reissued Patent: Mar. 1, 2016

(54) ROTATING CLIP ORTHODONTIC BRACKET

(71) Applicant: Ormco Corporation, Orange, CA (US)

(72) Inventor: Robert T. Rudman, Denver, CO (US)

(73) Assignee: Ormco Corporation, Orange, CA (US)

(21) Appl. No.: 14/258,944

(22) Filed: Apr. 22, 2014

Related U.S. Patent Documents

Reissue of:
(64) Patent No.: 8,162,660
Issued: Apr. 24, 2012
Appl. No.: 12/592,078
Filed: Nov. 20, 2009

(51) Int. Cl.
*A61C 3/00* (2006.01)
*A61C 7/28* (2006.01)

(52) U.S. Cl.
CPC ..... *A61C 7/285* (2013.01)

(58) Field of Classification Search
CPC ..... A61C 7/285
USPC ..... 433/10, 11, 13, 14; 40/10, 11, 13, 14
See application file for complete search history.

(56) References Cited

U.S. PATENT DOCUMENTS

| | | | | |
|---|---|---|---|---|
| 1,240,731 | A * | 9/1917 | Kinehan | 433/10 |
| 2,011,575 | A | 8/1935 | Ford | |
| 2,104,192 | A | 1/1938 | Ford | |
| 2,959,856 | A * | 11/1960 | Gurin | 433/22 |
| 3,084,437 | A | 4/1963 | Neger | |
| 3,158,934 | A | 12/1964 | Waldman | |
| 3,238,619 | A | 3/1966 | Brunson et al. | |
| 3,469,315 | A | 9/1969 | Russ | |
| 3,633,277 | A | 1/1972 | Reichel | |
| 3,793,730 | A | 2/1974 | Begg et al. | |
| 4,077,126 | A | 3/1978 | Pletcher | |
| 4,167,813 | A | 9/1979 | Forster | |
| 4,171,568 | A | 10/1979 | Forster | |
| 4,198,753 | A | 4/1980 | Forster | |
| 4,597,739 | A | 7/1986 | Rosenberg | |
| 4,664,626 | A | 5/1987 | Kesling | |
| 4,698,017 | A | 10/1987 | Hanson | |
| 4,712,999 | A | 12/1987 | Rosenberg | |
| 4,859,179 | A | 8/1989 | Kesling | |

(Continued)

FOREIGN PATENT DOCUMENTS

| | | | |
|---|---|---|---|
| CN | 201085695 | Y | 7/2008 |
| JP | 2003180712 | A | 7/2003 |
| WO | 2008130613 | A1 | 10/2008 |

OTHER PUBLICATIONS

Japanese Patent Office, Office Action in Japanese Patent Application No. 2012-539863, dated Feb. 20, 2014.

(Continued)

*Primary Examiner* — Cary Wehner
(74) *Attorney, Agent, or Firm* — Wood, Herron & Evans, LLP

(57) ABSTRACT

The present invention is directed to a locking orthodontic bracket that contains a mechanism that rotationally locks an orthodontic archwire fully or partially within the bracket archwire slot. The orthodontic bracket has a body containing a slot to receive an orthodontic archwire, wings for tying ligature wires, a base that is attachable to an orthodontic band or directly to a tooth surface and a central recess in the front surface of the body that contains the rotating clip device. The rotating clip device is rotated to enclose an orthodontic archwire within the slot.

44 Claims, 7 Drawing Sheets

(56) References Cited

U.S. PATENT DOCUMENTS

| | | | | |
|---|---|---|---|---|
| 4,867,678 | A | 9/1989 | Parker | |
| 4,917,602 | A | 4/1990 | Broussard | |
| 5,474,445 | A * | 12/1995 | Voudouris | 433/10 |
| 5,607,301 | A | 3/1997 | Roman | |
| 5,685,711 | A * | 11/1997 | Hanson | 433/11 |
| 5,823,771 | A | 10/1998 | Nord | |
| 5,857,850 | A | 1/1999 | Voudouris | |
| 6,071,118 | A | 6/2000 | Damon | |
| 6,071,119 | A | 6/2000 | Christoff et al. | |
| 6,247,923 | B1 | 6/2001 | Vashi | |
| 6,368,105 | B1 | 4/2002 | Voudouris et al. | |
| 6,506,049 | B2 | 1/2003 | Hanson | |
| 6,607,383 | B2 | 8/2003 | Abels et al. | |
| 6,616,445 | B2 | 9/2003 | Abels et al. | |
| 6,655,957 | B2 | 12/2003 | Abels et al. | |
| 6,655,958 | B2 | 12/2003 | Abels et al. | |
| 6,659,766 | B2 | 12/2003 | Abels et al. | |
| 6,659,767 | B2 | 12/2003 | Abels et al. | |
| 6,682,345 | B2 | 1/2004 | Kesling et al. | |
| 6,695,612 | B2 | 2/2004 | Abels et al. | |
| 6,733,286 | B2 | 5/2004 | Abels et al. | |
| 6,776,613 | B2 | 8/2004 | Orikasa | |
| 6,843,651 | B2 | 1/2005 | Orikasa | |
| 6,866,505 | B2 | 3/2005 | Senini | |
| 6,932,597 | B2 | 8/2005 | Abels et al. | |
| 6,942,483 | B2 | 9/2005 | Heiser | |
| 6,960,081 | B2 | 11/2005 | Abels et al. | |
| 6,960,808 | B2 | 11/2005 | Wang | |
| 7,063,531 | B2 | 6/2006 | Maijer et al. | |
| 7,094,052 | B2 | 8/2006 | Abels et al. | |
| 7,186,114 | B2 | 3/2007 | Navarro et al. | |
| 7,204,690 | B2 * | 4/2007 | Hanson | 433/10 |
| 7,210,927 | B2 | 5/2007 | Abels et al. | |
| 7,214,057 | B2 | 5/2007 | Voudouris | |
| 7,234,935 | B2 | 6/2007 | Abels et al. | |
| 7,247,018 | B2 | 7/2007 | Freeman, Jr. et al. | |
| 7,255,557 | B2 | 8/2007 | Forster | |
| 7,306,458 | B1 | 12/2007 | Lu | |
| 7,335,020 | B2 | 2/2008 | Castner et al. | |
| 7,442,039 | B2 | 10/2008 | Opin et al. | |
| 7,585,171 | B2 * | 9/2009 | Hagelganz et al. | 433/11 |
| 7,611,353 | B2 * | 11/2009 | Sommer | 433/10 |
| 7,621,743 | B2 | 11/2009 | Bathen et al. | |
| 7,674,110 | B2 * | 3/2010 | Oda | 433/10 |
| 7,695,277 | B1 | 4/2010 | Stevens | |
| 7,717,706 | B2 | 5/2010 | Forster | |
| 7,845,940 | B2 * | 12/2010 | Minium | 433/16 |
| 7,959,437 | B2 | 6/2011 | Zakhem et al. | |
| 7,963,768 | B2 * | 6/2011 | Hilliard | 433/11 |
| 8,162,660 | B2 | 4/2012 | Rudman | |
| 8,246,348 | B2 * | 8/2012 | Heiser | 433/10 |
| 2002/0119414 | A1 | 8/2002 | Orikasa | |
| 2002/0132206 | A1 | 9/2002 | Voudouris | |
| 2006/0051721 | A1 * | 3/2006 | Carriere Lluch | 433/10 |
| 2007/0009849 | A1 * | 1/2007 | Wool | 433/10 |
| 2007/0243497 | A1 * | 10/2007 | Voudouris | 433/10 |
| 2007/0259301 | A1 | 11/2007 | Hagelganz et al. | |
| 2007/0259304 | A1 | 11/2007 | Hagelganz et al. | |
| 2007/0269763 | A1 * | 11/2007 | Schendell-Groling | 433/10 |
| 2007/0281269 | A1 | 12/2007 | Forster | |
| 2009/0130621 | A1 | 5/2009 | Chikami | |
| 2010/0151403 | A1 * | 6/2010 | Tuneberg et al. | 433/10 |
| 2011/0081622 | A1 | 4/2011 | Mashouf | |
| 2011/0123942 | A1 | 5/2011 | Rudman | |
| 2011/0287378 | A1 | 11/2011 | Dupray et al. | |
| 2012/0129120 | A1 * | 5/2012 | Foerster | 433/11 |
| 2012/0288816 | A1 | 11/2012 | Dupray et al. | |

OTHER PUBLICATIONS

European Patent Office, Third Party Observation in European Patent Application No. 10831890.8, dated Sep. 24, 2014.

European Patent Office, Supplementary European Search Report in EP10831890.8 dated Nov. 24, 2014.

International Searching Authority, International Search Report and Written Opinion in International Application No. PT/US2014/042520 dated Sep. 25, 2014.

* cited by examiner

AMENDED
Fig. 2
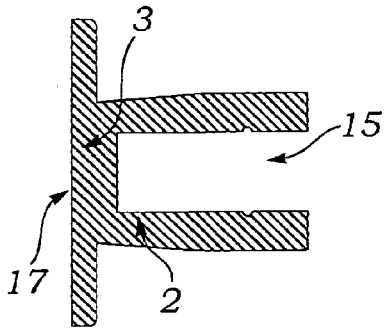
AMENDED
Fig. 3
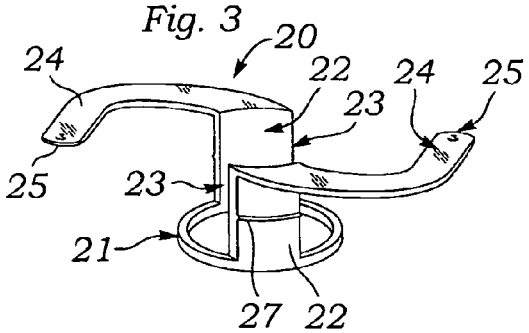
AMENDED
Fig. 4
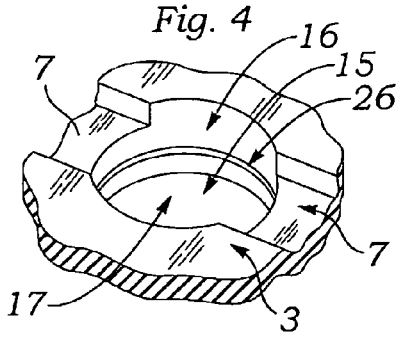

ROTATING CLIP ORTHODONTIC BRACKET

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*This application is a reissue application of U.S. Pat. No. 8,162,660 (application Ser. No. 12/592,078, filed Nov. 20, 2009), which is hereby incorporated by reference herein in its entirety for all purposes.*

FIELD OF THE INVENTION

The present invention is directed to a locking orthodontic bracket that contains a mechanism that rotationally locks an orthodontic archwire within the bracket archwire slot.

BACKGROUND OF THE INVENTION

Orthodontic brackets attached to teeth transmit forces, such as produced by an archwire, to move the teeth. Brackets usually contain an archwire slot for reception of the archwire. Orthodontic brackets today are typically bonded to a tooth or welded to an orthodontic band that is cemented to the tooth.

Brackets commonly use tie wings that project upwardly and downwardly in pairs at the top and bottom of the installed bracket, respectively. These wings permit the archwire to be held within the archwire slot of the bracket by means of a twisted wire (ligature) or an elastomeric o-ring. Currently there are varieties of brackets that are self-ligating. These self-ligating brackets have taken several forms.

U.S. Pat. No. 5,094,614 to Wildman, issued Mar. 10, 1992, discloses a sliding closure that engages the front of the archwire. The closure is recessed from the front or anterior surfaces of the disclosed bracket. These sliding closures are also found in U.S. Pat. No. 2,549,528 to Russell, U.S. Pat. No. 2,671,964 to Russell et al. and in U.S. Pat. No. 3,131,474 to Johnson. Sliding closures require the archwire also to be recessed within the archwire slot before the closure can be moved over the archwire making it very difficult for the user to visually confirm that the archwire is properly seated within the archwire slot. A conventional bracket has a visual front surface adjacent to the archwire slot making it easy to see if the archwire is seated in the archwire slot. This is not true in the recessed sliding closures. The actual archwire slot surface is beneath the sliding closure. Damon solved this problem in U.S. Pat. Nos. 5,275,557 (Jan. 4, 1994), 5,429,500 (Jul. 4, 1995) and 5,466,151 (Nov. 14, 1995).

An achievement of these patents is a ligating slide within a bracket that maintains the normal features of protruding tie wings or lugs and a closure in the form of a ligating slide that can complete a continuous tube surrounding the archwire when the closure is in a closed position. This can be achieved in a Siamese or twin bracket configuration without covering or interfering with projecting extensions on the bracket.

Pletcher, U.S. Pat. No. 5,322,435, discloses a locking slide member that is flat and guided by upright slots formed along both sides of the bracket and spanning the archwire slot thereby obscuring visual access to the critical corners of the archwire slots at the side edges of the bracket. Without this visual access being clear, one installing an archwire within a bracket cannot be certain as to proper seating of an archwire within the archwire slot before the slide cover is moved to a closed position. No tie wings or lugs are included in the illustrated bracket forms.

There is a modern esthetic requirement that the brackets be small. A drawback of many self-ligating brackets the locking covers increase the size of the bracket.

Damon, U.S. Pat. No. 6,071,118, discloses a sliding cover which gives visual access to the archwire slot, but have achieved the enclosure of the sliding cover by thickening the bracket in the gingival area A sliding spring cover, a hinged locking cover, a rotary sliding cover, a ball type rotatable cover etc. have been disclosed in different U.S. Patents. "Activa" produced by A Company, "Speed" and "Edgelock" produced by Ormco Corporation, and others are typical examples of ligature-less brackets that are commercially available.

Of all these different locking means a sliding closure has been considered desirable because it can be easily manipulated and it reduces the time required for opening and closing of the arch wire slot during periodic adjustments of the arch wire and provides more precise control of the archwire. There are other means that are more complex and difficult and expensive to manufacture. Springs used as locking means are not strong enough to hold the arch wire into the slot.

SUMMARY OF THE INVENTION

The present invention is directed to a locking orthodontic bracket. The locking orthodontic bracket is comprised of an orthodontic bracket that contains a rotating clip device for locking an orthodontic arch wire within the arch wire slot of the orthodontic bracket. The orthodontic bracket is comprised of a body containing a slot to receive an arch wire, wings for tying ligature wires, a base that is attachable to an orthodontic band or directly to a tooth surface and a central recess on the front surface of the body that extends inwardly towards the base of the bracket. The invention is a rotating clip for locking the orthodontic arch wire within the arch wire slot. Rotation of the clip in one direction leaves the archwire slot open for the insertion or removal of an archwire and rotation in the opposite direction locks the archwire in the archwire slot.

The rotating clip is comprised of a hollow cylindrical body with wings extending from the body. The cylindrical body has a circular base and two opposing vertical walls separated by opposing open sides. The opposing open sides allow for the passage of an archwire through the archwire slot and reduce friction during rotation of the rotating clip. The circular body is fitted and mechanically retained within the recess within the orthodontic bracket. The bracket recess is shaped and sized to receive the hollow circular body. The circular body and bracket recess may contain retentive devises such as circular grooves with matching ridges that also allow rotation of the rotating clip within the bracket recess. The wings extend laterally from the vertical cylindrical body over the surface of the orthodontic bracket. The tubular body is rotatable within the recess of the orthodontic bracket. The rotation moves the wings in a clockwise or counterclockwise motion. The bracket clip insertion hole can be slightly skewed from a perfect circle to allow friction grip when the clip is fully open or fully closed.

In a preferred embodiment, the tips of the wings enclose an orthodontic arch wire within the arch wire slot of the orthodontic bracket when the rotating clip is rotated counterclockwise. A clockwise rotation of the rotating clip opens the arch wire slot for placement or removal of the orthodontic arch wire. The strength transmitted to the wing tip is partially derived from the circular shape of the attached cylindrical body and the intimate fitting of the cylindrical body within the circular recess. The resulting strength is increased allowing the wings to be thinner which is advantageous for patient comfort. The underside of the wing, in one embodiment, has a bump that actively holds the archwire in the slot, as opposed to passively holding the archwire when the underside of the wing is flat. In another embodiment the rotating clip has two sets of wings wherein one pair actively engage the archwire when the rotating clip is rotated in one direction and passively holds the archwire when the rotating clip is rotated in the opposite direction. In another preferred embodiment, the locking clip wing is shaped to enclose most of the arch wire in the archwire slot. In another preferred embodiment, the underside of the locking clip wing contains a bevel to push the arch wire into the arch wire slot. In a further embodiment, the underside of the wing contains bumps for active clip design.

The bracket wall that retains the rotating clip remains open to self cleanse, reducing calculus build up and stuck moving parts. Tooth brush bristles can access the walls of bracket body. The bracket body design remains the same for both active and passive and active passive designs. The design allows the clinician to go from passive to active to conventional and back at any point in treatment. Height gauges may be used conventionally. The rotating clip does not interfere with anatomical structures, such as gums and other teeth, when in the open position. The rotating clip orthodontic bracket may be comprised of metal, plastic or ceramic or combinations thereof. Equivalent materials may be used. MIM technology can be used for the bracket body wherein retention for the clip is built within and there is a potential to use a breakaway design in MIM for one piece bracket body assembly. The door design will allow only the mesial or distal aspect of wing to be engaged on severely rotated teeth as the wing door can close around one wing while leaving the wire exiting the center of the bracket. The wire can be engaged from both the gingival and the occlusal in door design There is an ability to cut out the facial aspect of the bracket leaves latitude to maintain slot integrity while increasing bulk of metal in body and arms , but allowing slot cover part of clip to be thin for springiness (passive/active). It can be designed with reciprocal open and closed doors. There are many designs in the clip. The designs may be passive or active with the same bracket body which can be a stand-alone twin without the rotating clip. The wings may be altered for the use of non-binding power chains for closing spaces or rotating teeth. Horizontal slots can be added lateral surfaces of the wings. Vertical and horizontal channels may be placed for accessories such as hooks and rotators.

BRIEF DESCRIPTION OF THE DRAWINGS

FIG. 2 is a side view of the body of the self-ligating orthodontic bracket;

FIG. 3 is a perspective view of the rotating clip of the self-ligating orthodontic bracket;

FIG. 4 is a top perspective cutaway view of the body recess of the self-ligating orthodontic bracket;

DETAILED DESCRIPTION OF THE INVENTION

Figure 1:
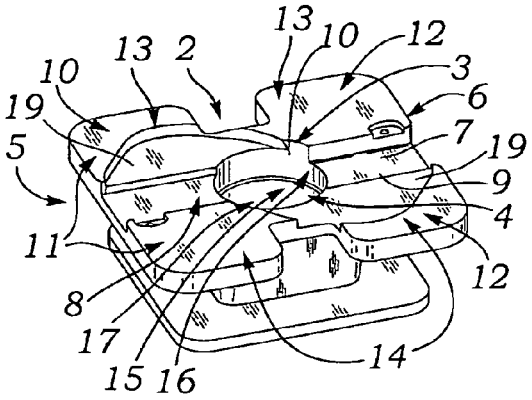
FIG. 1 is a top perspective view the body of the self-ligating orthodontic bracket.
Figure 5:
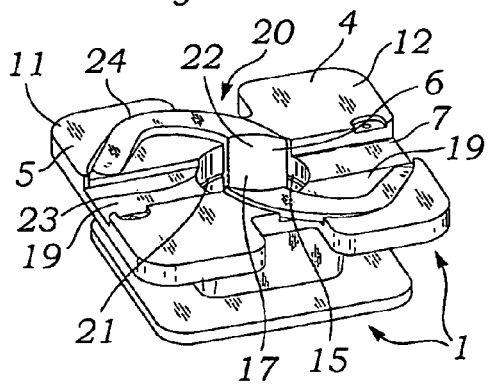
FIG. 5 is a top perspective view of the self-ligating orthodontic bracket in an open position.
Figure 6:
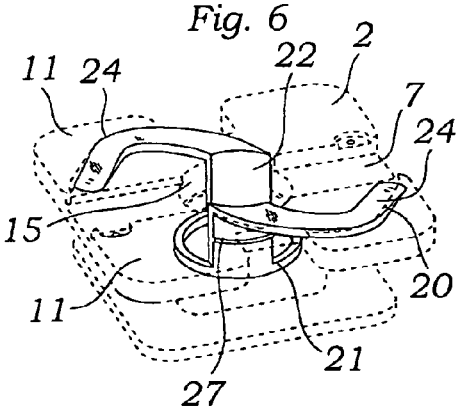
FIG. 6 is a top perspective internal view of the rotating clip resting within a cutout view of the body of the self-ligating orthodontic bracket.
Figure 7:
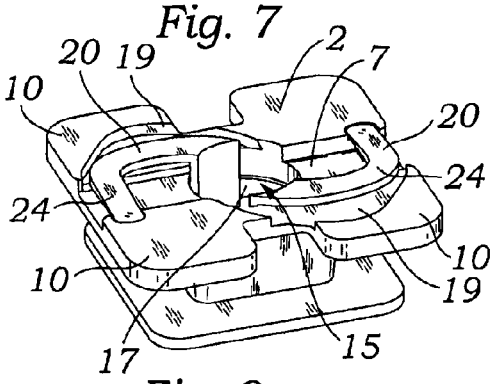
FIG. 7 is a top perspective view of the self-ligating orthodontic bracket with the rotating clip in a closed position.
Figure 8:
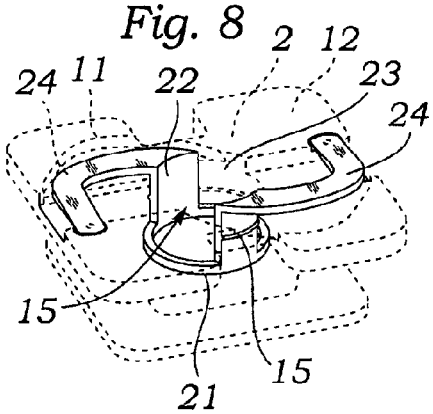
FIG. 8 is a top perspective internal view of the self-ligating orthodontic bracket with the rotating clip in a closed position.

The invention is comprised of a self-ligating orthodontic bracket assembly 1. FIG. 1 discloses a bracket body 2 with a back 3 and a front surface 4. The bracket body 2 has a left side 5 and right side 6. An archwire slot 7 extends from left 8 to right 9 on the front surface 3. Attached to the bracket body 2 are tie wings 10 positioned left 11 and right 12. The tie wings 10 extend outwardly from the top 13 and bottom 14. The front surface 4 of the bracket body 2 contains a cylindrical recess 15 with a circular wall 16 extending from a circular front 17 towards the body 2 back 3 ending in a circular floor. The tie wings 10 fit within front surface 4 recesses 19 in order to make the tie wings 10 flush with the bracket front surface 4. FIG. 2 shows the bracket body 2 in cross section. FIG. 3 discloses a rotating clip 20 which is attached into the cylindrical recess 15 of FIGS. 1 and 2. The rotating clip 20 has a circular base 21 with attached opposing columns 22 extending at right angles to the circular base 21. Between the opposing columns 22 are open opposing sides 23. Attached to each opposing column 22 free end is a c-shaped extension 24. The c-shaped extensions 24 each extend horizontally with a free end 25 and an underside 26. The attached opposing columns 22 have an outer circular periphery sized to fit the circular walls 16 of the circular recess 15. The circular periphery contains a circular groove 27. FIG. 4 is an enlarged view of the circular recess 15 disclosing the recess wall 16 with h a circular ring 26 which seats into the circular groove 27 of the rotating clip 20. The circular ring 26 circular groove 27 relationship allows the rotating clip 20 to be retained in the circular recess 15 and be free to rotate. FIG. 5 discloses the invention in its preferred embodiment. The rotating clip 20 is inserted in the cylindrical recess 15 of the bracket body 2 wherein the circular base 21 is seated against the circular floor 17. The c-shaped extensions 24 extend left 5 and right 6 on the surface of the front 4 of the bracket body 2. The open opposing sides 23 align with the horizontal archwire slot 7 allowing an archwire to o travel continuously from the left end 8 of the archwire slot 7 to the right end 9 of the archwire slot 7. FIG. 6 discloses the rotating clip 20 as it sits within the bracket body 2. A circular groove 27 is shown horizontally on the outer surface of the attached opposing column 22. FIGS. 5 and 6 show the rotating clip 20 in the open position wherein the c-shaped extensions 24 do not enclose the archwire slot 7. In this open position an archwire may be placed and removed from the archwire slot 7. In FIG. 7 the rotating clip 20 is rotated counterclockwise wherein the c-shaped extension 24 encloses the archwire slot 7 which would contain an archwire within the archwire slot 7. This is called the closed position. FIG. 8 discloses the details of the rotating clip 20 as it rests within the bracket body 2. The open opposing sides 23 between the opposing columns 22 allow an archwire 30 to go between the left end 8 and right end 9 of the archwire slot 7.

Figure 9:
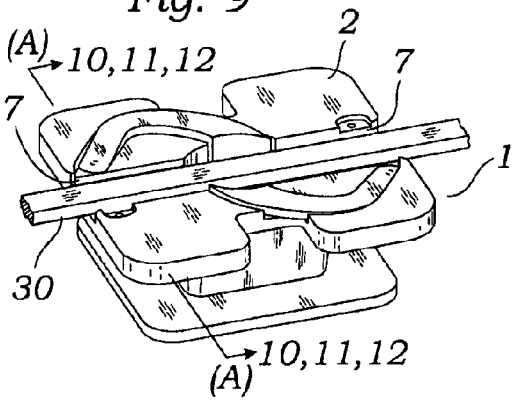
FIG. 9 is a top perspective view of the self-ligating orthodontic bracket with an archwire.
Figure 10A:
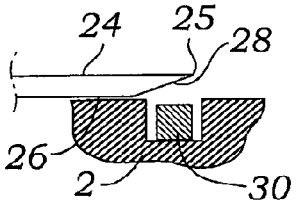
FIG. 10A is a fragmentary side view of the self-ligating orthodontic bracket of FIG. 9 through A-A with beveled ends of the rotating clip arms.
Figure 10B:
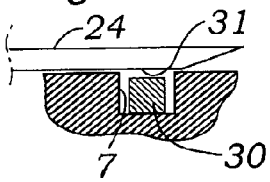
FIG. 10B is a fragmentary side view of the self-ligating orthodontic bracket of FIG. 9 through A-A with beveled ends of the rotating clip arms.
Figure 10C:
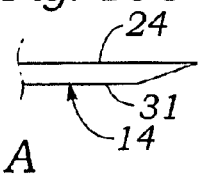
FIG. 10C is a fragmentary side view of the self-ligating orthodontic bracket of FIG. 9 through A-A with beveled ends of the rotating clip arms.
Figure 11A:
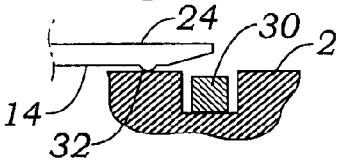
FIG. 11A is fragmentary side view of the self-ligating orthodontic bracket of FIG. 9 through A-A with active bumps underside the clip arm end.
Figure 12A:
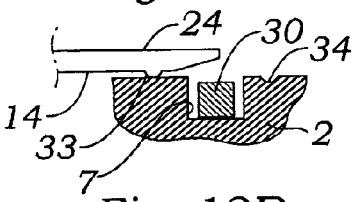
FIG. 12A is fragmentary side view of the self-ligating orthodontic bracket of FIG. 9 through A-A with retentive bumps underside the clip arm end.
Figure 11B:
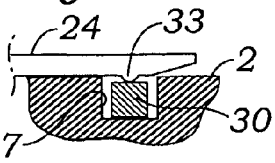
FIG. 11B is a fragmentary side view of the self-ligating orthodontic bracket of FIG. 9 through A-A with active bumps underside the clip arm end.
Figure 12B:
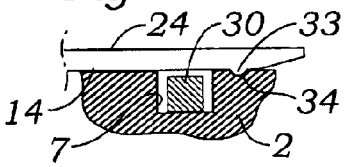
FIG. 12B is a fragmentary side view of the self-ligating orthodontic bracket of FIG. 9 through A-A with retentive bumps underside the clip arm end.
Figure 13:
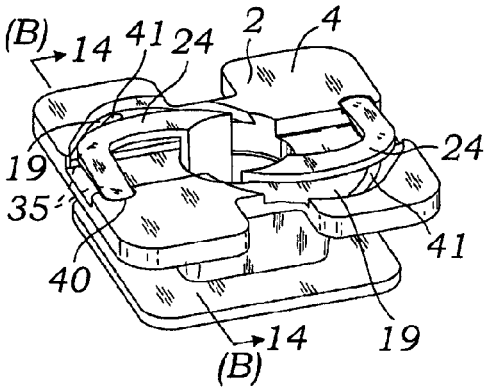
FIG. 13 is a top perspective view of the self-ligating orthodontic bracket with cutout channels.
Figure 14:
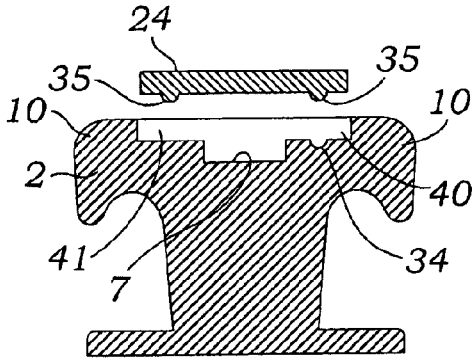
FIG. 14 is a cross-sectional view of the self-ligating orthodontic bracket of FIG. 13 through B-B.
Figure 15:
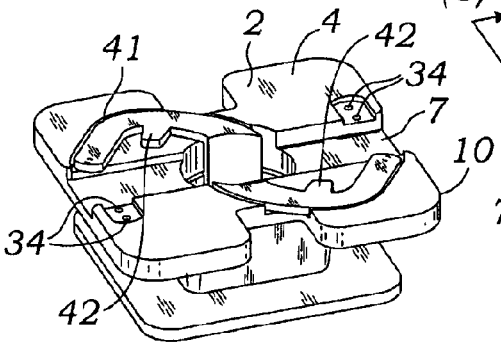
FIG. 15 is a top perspective view of the self-ligating orthodontic bracket with extension tabs in an open position.
Figure 16:
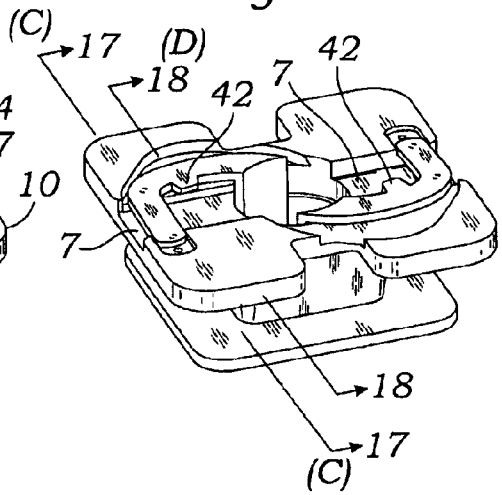
FIG. 16 is a top perspective view of the self-ligating orthodontic bracket with extension tabs in a closed position.
Figure 17A:
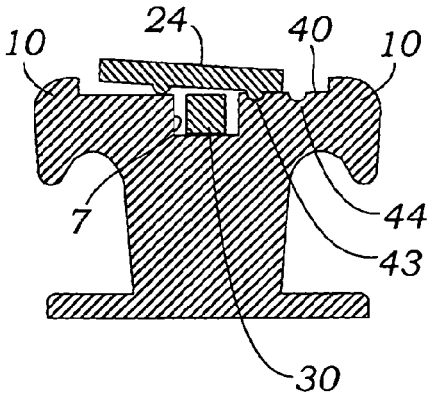
FIG. 17A is cross-sectional view of FIG. 16 through C-C.
Figure 17B:
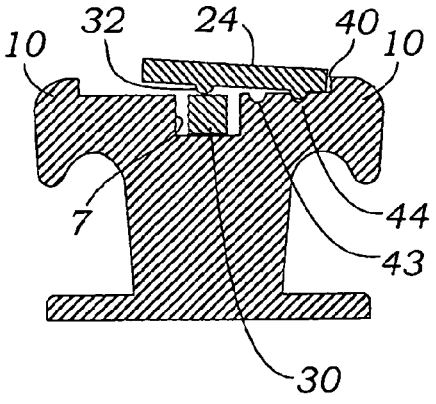
FIG. 17B is a cross-sectional view of FIG. 16 through C-C.
Figure 18A:
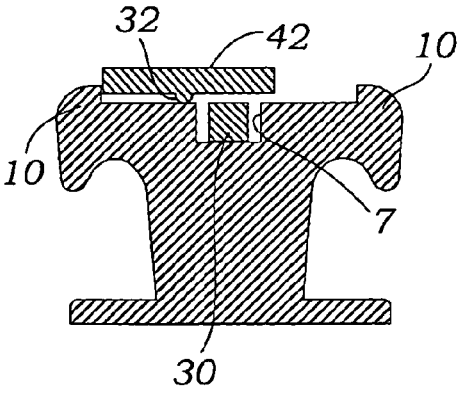
FIG. 18A is cross-sectional view of FIG. 16 through D-D.
Figure 18B:
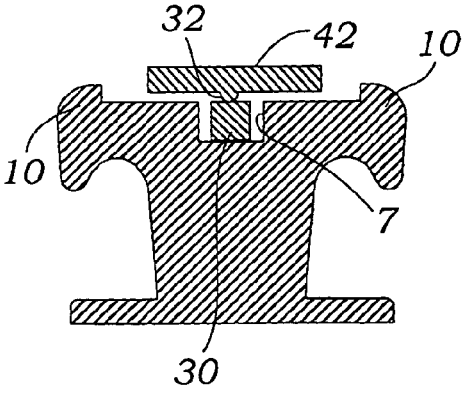
FIG. 18B is a cross-sectional view of FIG. 16 through D-D.
Figure 19:
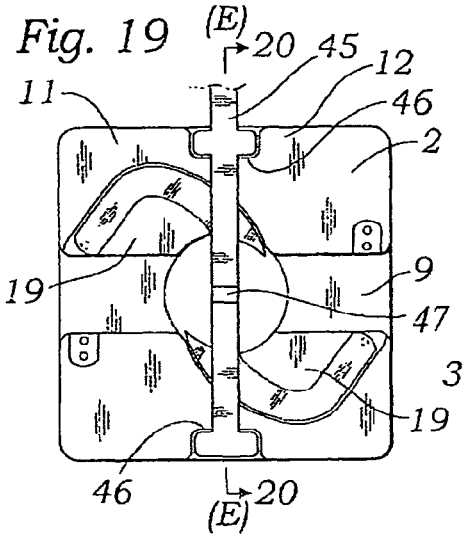
FIG. 19 is a top perspective view of the self-ligating orthodontic bracket with an index pin.
Figure 20:
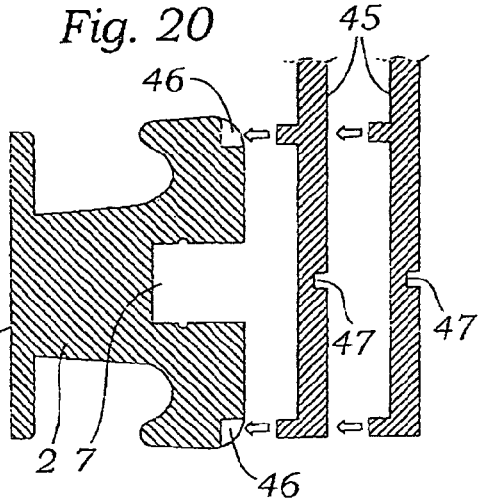
FIG. 20 is a cross-sectional view of the self-ligating orthodontic bracket of FIG. 19 through E-E.

FIG. 9 discloses the rotating clip orthodontic bracket 1 with the rotating clip 20 in an open position and an archwire 30 in the archwire slot 7. FIGS. 10A are cross sections of FIG. 9 through points A . . . A. The c-shaped extension 24 rests upon the bracket body 2 and has a free end 25 with a beveled leading edge 28 underside 26 wherein the beveled leading edge 28 facilitates the c-shaped extension 24 sliding over the archwire 30 as shown in FIG. 10B. FIG. 10C is a cross-section of the c-shaped extension 24 with a bottom side 14 that is flat 31. In FIG. 10B, the flat 31 bottom side 14 holds the archwire 30 passively in the archwire slot 7. FIG. 11A discloses the cross-section of FIG. 9 wherein the bottom 14 of the c-shaped extension 24 has an active bump 33 that holds the archwire 30 actively in the archwire slot 7 as shown in FIG. 11B. In FIG. 12A, the c-shaped extension 24 bottom 14 has a retentive bump 33 and a dimple 34 in the bracket body 2. The rotating clip 20 is held in a closed position when the retentive bump 33 is seated in the dimple, FIG. 12B. FIG. 13 discloses underside bumps 19, 35 that fit into a recess channel 41 on the bracket front 4. The recess channel 41 guides the round bumps 35 during the rotation of the rotating clip 20. FIG. 14 is a cross-section through B-B of FIG. 13. A round bump 35 on the bottom surface of the c-shaped extension 24 fits into the cutout channel 41 of the bracket body 41 and a cutout channel 40 for receiving the free end of the c-shaped extension 24 contains a dimple 34 for receiving the dimple 34 on the bottom side of the c-shaped extension 24. FIG. 15 discloses a tab 42 on each c-shaped extension 24 extending towards the archwire slot 7. The tab 42 bottom may be smooth or may contain a bump 35. FIG. 16 shows the same rotating clip orthodontic bracket 1, as in FIG. 15, wherein the C-shaped extension 24 is in a first closed position. The first closed position is where the underside retentive bump 35 shown in FIG. 14 is seated in the dimple 34 closest to the archwire slot 7 as shown in FIG. 15. FIG. 16 discloses the tabs 42 not covering the archwire slot 7. When the c-shaped extension 24 is rotated further counterclockwise into the second dimple, FIG. 15, 34, the tabs 42 enclose the archwire slot 7. FIG. 17A shows a cross-section of FIG. 16 through C-C wherein two dimples, No. 1 dimple 43 and No. 2 dimple 44, are in the cutout channel 40 in the first position. FIG. 17B discloses the second position wherein the round bump 35 is in the No. 2 dimple 44 which places a dimple over the archwire 30 which holds the archwire 30 actively. FIGS. 18A and 18B show FIG. 16 through D-D. FIG. 18A discloses the tab 42 with the smooth underside 26 of the tab 42 above the archwire 30, holding the archwire 30 passively. FIG. 18B shows the tab 42 further advanced over the archwire wherein the underside 26 of the tab 42 has a bump 32 that actively holds the archwire 30. FIGS. 19 and 20 disclose an index pin 45.

When orthodontic brackets are placed upon teeth they are ideally positioned with the bracket slot a predetermined distance from the incisal edge or occlusal surface of the tooth. In addition, the horizontal direction of the orthodontic bracket is placed at a right angle to the long axis of the tooth. An index pin 45, FIG. 19, is a pin vertically attached to the orthodontic bracket that helps visualize the correct long axis placement of the orthodontic bracket during its placement. FIG. 19 shows the index pin 45 attached to the self-ligating orthodontic assembly 1 in seats 46 between the left 11 and right 12 tie wings 10. FIG. 20 is a cross section through E-E of FIG. 19. In addition, a measuring notch 47 shows the position of the underlying archwire slot 7 that is helpful in the vertical positioning of the orthodontic bracket.

Figure 21:
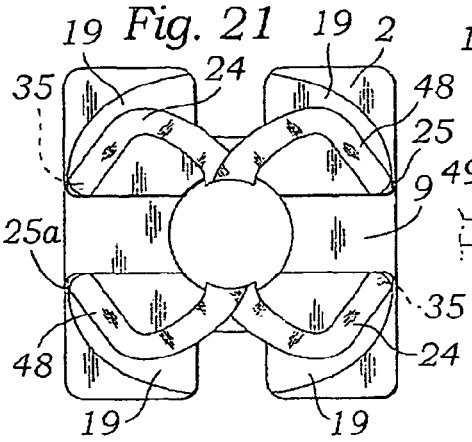
FIG. 21 is a top perspective view of the self-ligating orthodontic bracket with a second pair of c-shaped extensions, all extensions in the open position.
Figure 22:
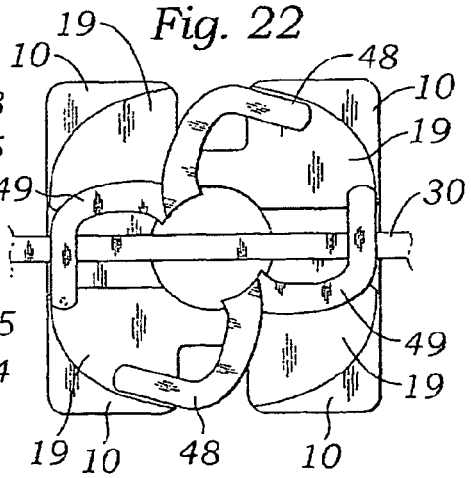
FIG. 22 is a top perspective view of the self-ligating orthodontic bracket with a second pair of c-shaped extensions wherein the rotating clip is turned counterclockwise into a closed position.
Figure 23:
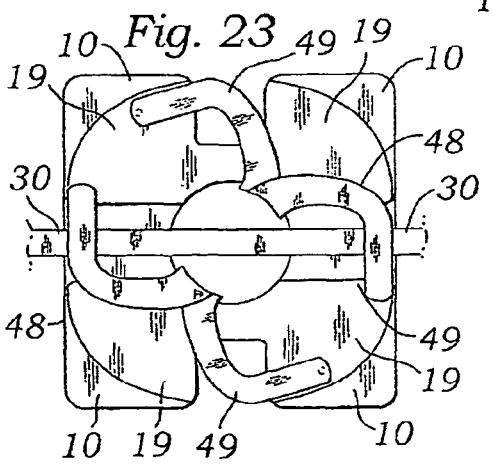
FIG. 23 is a top perspective view of the self-ligating orthodontic bracket with a second pair of c-shaped extensions wherein the rotating clip is turned clockwise into a closed position.
Figure 24:
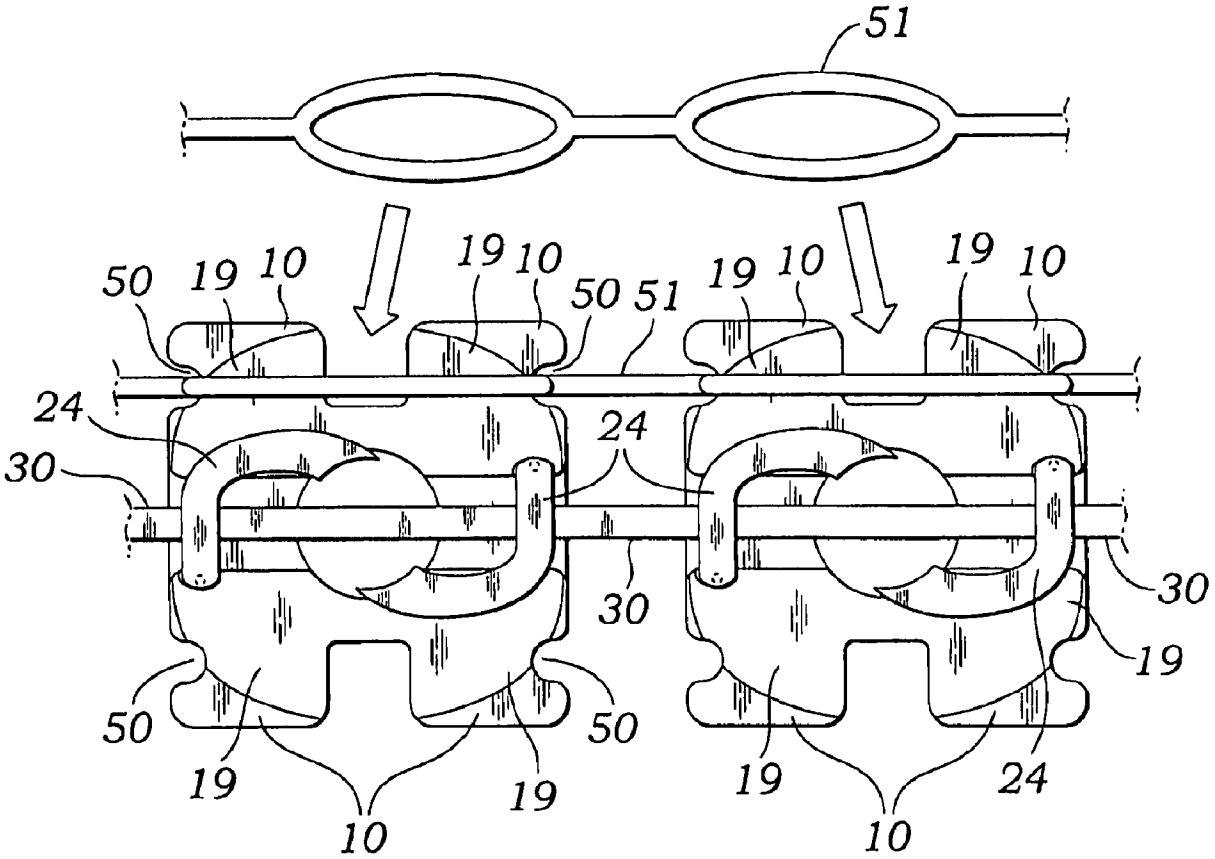
FIG. 24 is top perspective views of a pair of self-ligating orthodontic brackets with notches and attached elastomeric chains.
Figure 25:
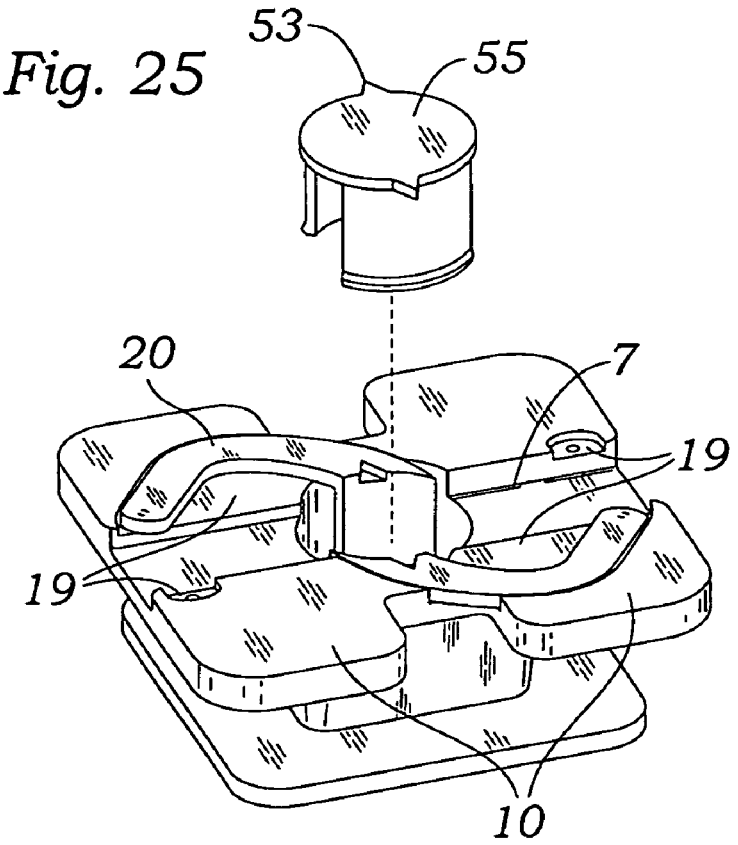
FIG. 25 is a top perspective view of the self-ligating orthodontic bracket with a n attachable clip.
Figure 26:
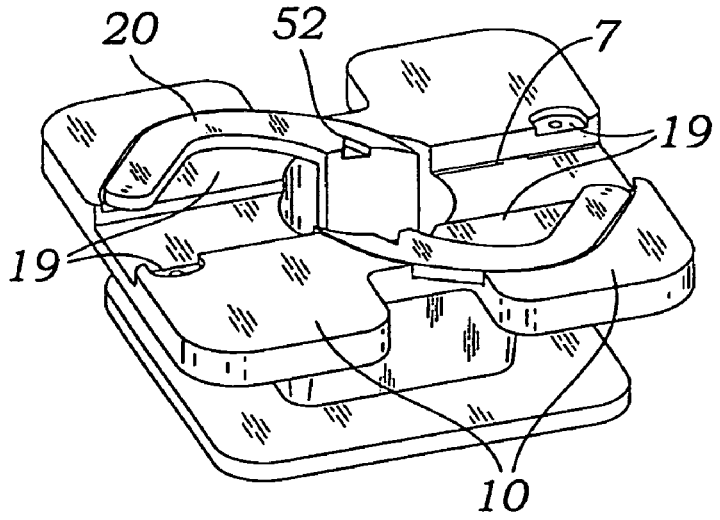
FIG. 26 is a top perspective view of the self-ligating orthodontic bracket with an attachable clip and anti-rotation notches.

FIGS. 21-23 disclose another preferred embodiment of the invention wherein there is a second pair of c- shaped extensions 24. FIG. 21 shows the self-ligating orthodontic bracket assembly 1 in an open position. The first c-shaped extensions 49 have a bump 35 on the under side and the second c-shaped extensions have a flat underside 25a. FIG. 22 shows the rotating clip 20 rotated counterclockwise wherein the underside bumps 35 engage and hold the archwire 30 actively. FIG. 23 shows the rotating clip 20 rotated clockwise wherein the second c-shaped extensions 48 have a flat undersides 25a that engage and hold the archwire 30 passively. FIG. 24 discloses a modification of the bracket wings wherein the upper and lower left wings have horizontal notches extending to the body center from the left of the bracket and the upper and lower right wings have horizontal notches 50 extending to the center 4 of the bracket body 2 , the notches 50 allow attachment of orthodontic elastomeric power chains 51 to the upper wings 13 only or to the lower wings 14 only. Elastomeric chains 51 are a series of connected islets made from an elastic material. The elastomeric chains 51 are normally used to close spaces between teeth rotate teeth and maintain the lack of spacing between teeth. The elastomeric chains 51 normally circle all four bracket wings 10 and secure the archwire 30 in the archwire slot 7. In the present invention, the elastomeric chain 51 does not enclose the archwire. The elastomeric chain 51 can be changed without disturbing the archwire 30 or, conversely, the archwire 30 can be changed without disturbing the elastomeric chain 51.

The invention may include integral hooks for rubber band wear by the patient. In the alternative, channels may be placed in the invention to receive removable hooks for rubber band and other attachments. The rotating clip orthodontic bracket may be comprised of a variety of materials including metal, plastic and ceramic and decorative forms consisting of a variety of colors, glow-in-the-dark and LED lights which may be activated by the patient tapping their teeth together.

The invention, as described, is not limited to the specific embodiments described as these are preferred embodiments. The invention is claimed in any of its modifications within the proper scope of its claims.

What is claimed is:

[1. A rotating clip orthodontic bracket comprising:

an orthodontic bracket comprising a body, the body having a back, a front with a center, left and right sides, a top and a bottom, the body front contains an archwire slot extending horizontally left side to right side shaped to receive an orthodontic archwire with right and left ends, left and right tie wings at the top and bottom body for tie wires or elastomeric ties for securing an archwire within the archwire slot;

a cylindrical recess with walls in the center of the body front of the orthodontic bracket wherein the cylindrical recess is open on the body front and extends towards the body back wherein the cylindrical recess ends with a circular floor; and a rotating clip within the cylindrical recess for securing orthodontic archwires comprised of a circular base, two attached opposing columns separated by open opposing sides which allow the passage of an archwire through the archwire slot, each column supporting a c-shaped extension with a free end and an underside facing the bracket front wherein the circular base is fitted to the wall adjacent to the circular floor, the opposing columns are fitted to the cylindrical recess walls and the c-shaped extensions extend on the bracket front in opposing directions, the clip is fitted in the cylindrical recess and when the clip is rotated in a clockwise rotation position the bracket slot is open allowing the insertion and removal of an archwire and when the clip is rotated in a counterclockwise position the c-shaped extensions retain the archwire within the archwire slot at the right and left ends of the archwire slot.]

[2. The rotating clip orthodontic bracket of claim 1 further comprising top and bottom index pin notches in the center of the front of the bracket between the left and right tie wings wherein an index pin with a measuring notch is placed to guide the placement of the orthodontic bracket on a tooth.]

[3. The rotating clip orthodontic bracket of claim 1 wherein the c-shaped extensions free end undersides each contain a bump projecting downwards towards the front of the body of the orthodontic bracket, the front of the body contains dimples shaped to receive the respective bumps, the dimples are placed to receive the respective dimples and lock the c-shaped extension in archwire slot closed position when the rotating clip is rotated counterclockwise and lock the c-shaped extension in the archwire slot open position when the rotating clip is rotated clockwise.]

[4. The rotating clip orthodontic bracket clip of claim 1 wherein the c-shaped extensions free ends each have a surface facing the front of the body of the orthodontic bracket, this surface is beveled towards the c-shaped extension free end which facilitates sliding the c-shaped extension free end over an orthodontic archwire that has been placed in the archwire slot.]

[5. The rotating clip orthodontic bracket of claim 1 wherein the c-shaped extensions have flat undersides which enclose the archwire passively in the archwire slot when the rotating clip is rotated counterclockwise.]

[6. The rotating clip orthodontic bracket of claim 1 wherein the c-shaped extensions have round bumps extruding from their undersides near their free ends which press down and hold the archwire actively in the archwire slot when the rotating clip is rotated counterclockwise.]

[7. The rotating clip orthodontic bracket of claim 1 wherein the bracket body face has cutouts adjacent to the archwire slot shaped to receive the free ends of the c-shaped extensions which have underside bumps in their free ends and middles and a channel on the bracket body face under each c-shaped extension to guide the middle underside bumps during the rotation of the rotating clip.]

[8. The rotating clip orthodontic bracket of claim 1 wherein there are four c-shaped extensions, two opposing extensions with flat undersides which enclose the archwire passively when the rotating clip is rotated counterclockwise and two c-shaped extensions with underside bumps which enclose the archwire actively in the archwire slot when the rotating clip is turned clockwise.]

[9. The rotating clip orthodontic bracket of claim 1 wherein the c-shaped extensions each have a middle which contain an extension tab which projects towards the archwire slot, the extension tab encloses the archwire when the rotating clip is in the closed position thus increasing the closure of the archwire in the archwire slot.]

[10. The rotating clip orthodontic bracket of claim 1 wherein the top and bottom left and right wings have horizontal notches extending to the body center from the left of the bracket and the upper and lower right wings have horizontal notches extending to the body center from the right of the bracket, the notches allow attachment of orthodontic elastomeric power chains to the upper wings only or to the lower wings only which prevents the elastomeric chains from contacting and binding the archwire and allows the archwire to be placed or removed without removing the elastomeric chain.]

[11. The rotating clip orthodontic bracket of claim 1 wherein there are upper and lower index pin notches positioned between adjacent tie wings to receive an index pin with a horizontal measuring notch for positioning the orthodontic bracket upon a tooth.]

[12. The rotating clip orthodontic bracket of claim 1 wherein the cylindrical wall has a circular ring and the attached columns of the rotating clip has a circular groove, wherein when the circular ring is seated in the circular groove the rotating clip is allowed to rotate without being unseated from the cylindrical recess.]

[13. The rotating clip orthodontic bracket of claim 1 which is comprised of a variety of materials including metal, plastic or ceramic and decorative forms comprising a variety of colors, glow-in-the-dark and LED lights which may be activated by the patient tapping their teeth together.]

[14. The rotating clip orthodontic bracket comprising:

an orthodontic bracket comprising a body, the body having a back, a front with a center, left and right sides, a top and a bottom, the body front contains an archwire slot extending horizontally left side to right side shaped to receive an orthodontic archwire with right and left ends, left and right tie wings at the top and bottom body for tie wires or elastomeric ties for securing an archwire within the archwire slot;

a cylindrical recess with walls in the center of the body front of the orthodontic bracket wherein the cylindrical recess is open on the bracket body front and extends towards the bracket body back wherein the cylindrical recess ends with a circular floor; and a rotating clip within the cylindrical recess for securing orthodontic archwires comprised of a circular base, two attached opposing columns separated by open opposing sides which allow the passage of an archwire through the archwire slot, the columns supporting first and second opposing sets of c-shaped extensions, the first set with a c-shaped extension adjacent to the top left tie wing, wherein the first opposing c-shaped extension end undersides each have a bump and the second opposing c-shaped extension end undersides are each flat, the circular base is fitted to the cylindrical recess wall adjacent to the circular floor, the opposing columns are fitted to the cylindrical recess walls and the c-shaped extensions extend on the bracket front in opposing directions, the clip is fitted in the cylindrical recess and when the rotating clip is in a center position the bracket slot is open allowing the insertion and removal of an archwire in the archwire slot, when the rotating clip is rotated in a counterclockwise position the bumps, on the underside of the c-shaped extensions, push on the archwire to retain the archwire actively within the archwire slot at the right and left ends of the archwire slot, when the rotating clip is rotated clockwise the flat undersurface of the c-shaped extensions push on the archwire holding hold the archwire passively in the archwire slot.]

[15. The rotating clip orthodontic bracket of claim 14 further comprising top and bottom index pin notches positioned between adjacent tie wings in the center of the front of the bracket body wherein an index pin with a measuring notch is placed to guide the placement of the orthodontic bracket on a tooth.]

[16. The rotating clip orthodontic bracket clip of claim 14 wherein the c-shaped extensions free ends each have a surface facing the front of the body of the orthodontic bracket, this surface is beveled towards the free ends which facilitates sliding the c-shaped end over an orthodontic archwire that has been placed in the archwire slot.]

[17. The rotating clip orthodontic bracket of claim 14 wherein the bracket face has cutouts adjacent to the archwire slot shaped to receive c-shaped extension ends with underside bumps and a channel on the bracket face with adjacent underside bumps on the c-shaped extensions wherein the cutouts guide the underside bumps during the rotation of the rotating clip.]

[18. The rotating clip orthodontic bracket of claim 14 wherein the c-shaped extensions have a middle which contain an extension tab which projects towards the archwire slot, the extension tab encloses the archwire when the rotating clip is in the closed position thus increasing the closure of the archwire in the archwire slot.]

[19. The rotating clip orthodontic bracket of claim 14 wherein the top left and right wings have horizontal notches extending to the body center from the left of the bracket and the lower right and left wings have horizontal notches extending to the body center from the of the bracket, the notches allow attachment of orthodontic elastomeric power chains to the upper wings only or to the lower wings only.]

[20. The rotating clip orthodontic bracket of claim 14 wherein there are upper and lower index pin notches to receive an index pin with a horizontal measuring notch for positioning the orthodontic bracket upon a tooth.]

[21. The rotating clip orthodontic bracket of claim 14 wherein the cylindrical wall has a circular ring and the attached columns of the rotating clip has a circular groove, when circular ring is seated in the circular groove the rotating clip is allowed to rotate without being unseated from the cylindrical recess.]

[22. The rotating clip orthodontic bracket of claim 14 which is comprised of a variety of materials selected from the group consisting of metal, plastic and ceramic and decorative forms comprising a variety of colors, glow-in-the-dark and LED lights which may be activated by the patient tapping their teeth together.]

[23. A method of straightening teeth using the rotating clip orthodontic bracket of claim 14, comprising:

attaching a rotating orthodontic bracket to a tooth;

rotating the orthodontic bracket rotating clip to an archwire slot open position;

placing an orthodontic archwire into the archwire slot;

enclosing the archwire by rotating the rotating clip until the archwire is enclosed within the archwire slot;

opening the orthodontic archwire slot by rotating the rotating clip into an archwire slot is open; and removing the orthodontic archwire.]

*24. A self-ligating orthodontic bracket comprising:*

*a bracket body including an archwire slot; and*

*a clip including a clip body and at least a first extension that extends laterally outward from the clip body, the clip being configured to rotate between an opened position and a first closed position and a second closed position in both of which the first extension retains an archwire in the archwire slot, wherein when the clip is rotated to the first closed position, the first extension actively ligates the archwire and when the clip is rotated to the second closed position, the first extension passively ligates the archwire, wherein the clip rotates about an axis of rotation that lies within the archwire slot.*

*25. The self-ligating orthodontic bracket of claim 24, wherein the first extension is generally C-shaped.*

*26. The self-ligating orthodontic bracket of claim 24, wherein the first extension includes a protrusion that is configured to project into the archwire slot when the clip is rotated to the first closed position to actively ligate the archwire, and when the clip is rotated to the second closed position, the protrusion does not project into the archwire slot.*

*27. The self-ligating orthodontic bracket of claim 26, wherein the bracket body further includes an indentation and when the clip is in the second closed position, the protrusion is received in the indentation.*

*28. The self-ligating orthodontic bracket of claim 24, wherein the bracket body includes a recess that is open to a front surface of the bracket body and that defines the axis of rotation.*

*29. The self-ligating orthodontic bracket of claim 24, wherein the clip body includes opposing walls that define opposing openings therebetween and the first extension extends from one opposing wall, and when the clip is in the opened position, the opposing openings generally align with the archwire slot so that the archwire passes through the opposing openings.*

*30. The self-ligating orthodontic bracket of claim 24, wherein the first extension includes a beveled leading edge.*

*31. A self-ligating orthodontic bracket comprising:*

*a bracket body including an archwire slot and a recess open to a front surface of the bracket body; and*

*a clip including a clip body that is configured to fit within the recess and at least a first extension that extends laterally outward from the clip body and has a protrusion that projects into the archwire slot, the clip being configured to rotate between an opened position and a first closed position and a second closed position in both of which the first extension retains an archwire in the archwire slot, wherein rotation of the clip from the opened position to the first closed position positions the first extension so that the protrusion projects into the archwire slot to actively ligate the archwire, and by further rotation in the same direction from the first closed position to the second closed position, the first extension spans the archwire slot and moves the protrusion out of the archwire slot to passively ligate the archwire.*

*32. The self-ligating orthodontic bracket of claim 31, wherein the first extension is generally C-shaped.*

*33. The self-ligating orthodontic bracket of claim 31, wherein the bracket body further includes an indentation and when the clip is in the second closed position, the protrusion is received in the indentation.*

*34. The self-ligating orthodontic bracket of claim 31, wherein the clip includes a second extension extending laterally outward from the clip body, and the second extension retains the archwire in the archwire slot when the clip is in each of the first closed position and the second closed position.*

*35. The self-ligating orthodontic bracket of claim 34, wherein the second extension has a second protrusion and when the clip is rotated to the first closed position, the second protrusion projects into the archwire slot and actively ligates the archwire, and by further rotation in the same direction from the first closed position to the second closed position, the second extension spans the archwire slot and moves the second protrusion out of the archwire slot.*

*36. The self-ligating orthodontic bracket of claim 35, wherein the bracket body further includes a second indentation and the second protrusion is received in the second indentation when the clip is rotated to the second closed position.*

*37. The self-ligating orthodontic bracket of claim 34, wherein each of the first extension and the second extension is generally C-shaped so that in each of the first closed position and the second closed position a portion of the first and second extensions is transverse to the archwire slot proximate a mesial side and a distal side of the bracket body, respectively.*

*38. The self-ligating orthodontic bracket of claim 31, wherein the recess defines an axis of rotation and the axis of rotation intersects the archwire slot.*

*39. The self-ligating orthodontic bracket of claim 31, wherein the clip body includes opposing walls that define opposing openings therebetween and the first extension extends from one opposing wall, and when the clip is in the opened position, the opposing openings generally align with the archwire slot so that the archwire passes through the opposing openings.*

*40. A self-ligating orthodontic bracket comprising:*

*a bracket body including an archwire slot and a recess, each of the archwire slot and the recess being open to a front surface of the bracket body; and*

*a clip including a clip body that is configured to fit within the recess and a first extension and a second extension each extending laterally outward from the clip body, the clip being configured to rotate between an opened position and a first closed position and a second closed position in both of which the first extension and the second extension retain an archwire in the archwire slot, wherein when the clip is rotated to the first closed position, the first extension and the second extension actively ligate the archwire and when the clip is rotated to the second closed position, the first extension and the second extension passively ligate the archwire.*

*41. The self-ligating orthodontic bracket of claim 40, wherein the first extension includes a first protrusion and the second extension includes a second protrusion, and when the clip is rotated to the first closed position, the first protrusion and the second protrusion project into the archwire slot and actively ligate the archwire, and when the clip is rotated to the second closed position, the first protrusion and the second protrusion do not project into the archwire slot.*

*42. The self-ligating orthodontic bracket of claim 41, wherein the bracket body further includes at least one indentation and when the clip is in the second closed position, the first protrusion is received in the at least one indentation.*

*43. The self-ligating orthodontic bracket of claim 40, wherein each of the first extension and the second extension is generally C-shaped so that in each of the first closed position and the second closed position a portion of the first and second extensions is transverse to the archwire slot proximate a mesial side and a distal side of the bracket body, respectively.*

*44. The self-ligating orthodontic bracket of claim 40, wherein the recess defines an axis of rotation and the axis of rotation intersects the archwire slot.*

*45. A rotating clip orthodontic bracket comprising:*

*an orthodontic bracket comprising a body, the body having a back, a front with a center, left and right sides, a top and a bottom, the body front contains an archwire slot extending horizontally left side to right side shaped to receive an orthodontic archwire with right and left ends, left and right tie wings at the top and bottom body for tie wires or elastomeric ties for securing an archwire within the archwire slot;*

*a cylindrical recess with walls in the center of the body front of the orthodontic bracket wherein the cylindrical recess is open on the body front and extends towards the body back wherein the cylindrical recess ends with a circular floor; and*

*a rotating clip within the cylindrical recess for securing orthodontic archwires comprised of a circular base, two attached opposing columns separated by open opposing sides which allow the passage of an archwire through the archwire slot, each column supporting a C-shaped extension with a free end and an underside facing the bracket front wherein the circular base is fitted to the wall adjacent to the circular floor, the opposing columns are fitted to the cylindrical recess walls and the C-shaped extensions extend on the bracket front in opposing directions, the clip is fitted in the cylindrical recess and when the clip is rotated in a clockwise rotation position the bracket slot is open allowing the insertion and removal of an archwire and when the clip is rotated in a counterclockwise position the C-shaped extensions retain the archwire within the archwire slot at the right and left ends of the archwire slot.*

*46. The rotating clip orthodontic bracket of claim 45 further comprising top and bottom index pin notches in the center of the front of the bracket between the left and right tie*

*wings wherein an index pin with a measuring notch is placed to guide the placement of the orthodontic bracket on a tooth.*

*47. The rotating clip orthodontic bracket of claim 45 wherein the c-shaped extensions free end undersides each contain a bump projecting downwards towards the front of the body of the orthodontic bracket, the front of the body contains dimples shaped to receive the respective bumps, the dimples are placed to receive the respective dimples and lock the c-shaped extension in archwire slot closed position when the rotating clip is rotated counterclockwise and lock the c-shaped extension in the archwire slot open position when the rotating clip is rotated clockwise.*

*48. The rotating clip orthodontic bracket clip of claim 45 wherein the c-shaped extensions free ends each have a surface facing the front of the body of the orthodontic bracket, this surface is beveled towards the c-shaped extension free end which facilitates sliding the c-shaped extension free end over an orthodontic archwire that has been placed in the archwire slot.*

*49. The rotating clip orthodontic bracket of claim 45 wherein the c-shaped extensions have flat undersides which enclose the archwire passively in the archwire slot when the rotating clip is rotated counterclockwise.*

*50. The rotating clip orthodontic bracket of claim 45 wherein the c-shaped extensions have round bumps projecting from their undersides near their free ends which press down and hold the archwire actively in the archwire slot when the rotating clip is rotated counterclockwise.*

*51. The rotating clip orthodontic bracket of claim 45 wherein the bracket body face has cutouts adjacent to the archwire slot shaped to receive the free ends of the c-shaped extensions which have underside bumps in their free ends and middles and a channel on the bracket body face under each c-shaped extension to guide the middle underside bumps during the rotation of the rotating clip.*

*52. The rotating clip orthodontic bracket of claim 45 wherein there are four c-shaped extensions, two opposing extensions with flat undersides which enclose the archwire passively when the rotating clip is rotated counterclockwise and two c-shaped extensions with underside bumps which enclose the archwire actively in the archwire slot when the rotating clip is turned clockwise.*

*53. The rotating clip orthodontic bracket of claim 45 wherein the c-shaped extensions each have a middle which contain an extension tab which projects towards the archwire slot, the extension tab encloses the archwire when the rotating clip is in the closed position thus increasing the closure of the archwire in the archwire slot.*

*54. The rotating clip orthodontic bracket of claim 45 wherein the top and bottom left and right wings have horizontal notches extending to the body center from the left of the bracket and the upper and lower right wings have horizontal notches extending to the body center from the right of the bracket, the notches allow attachment of orthodontic elastomeric power chains to the upper wings only or to the lower wings only which prevents the elastomeric chains from contacting and binding the archwire and allows the archwire to be placed or removed without removing the elastomeric chain.*

*55. The rotating clip orthodontic bracket of claim 45 wherein there are upper and lower index pin notches positioned between adjacent tie wings to receive an index pin with a horizontal measuring notch for positioning the orthodontic bracket upon a tooth.*

*56. The rotating clip orthodontic bracket of claim 45 wherein the cylindrical wall has a circular ring and the attached columns of the rotating clip has a circular groove, wherein when the circular ring is seated in the circular groove the rotating clip is allowed to rotate without being unseated from the cylindrical recess.*

*57. The rotating clip orthodontic bracket of claim 45 which is comprised of a variety of materials including metal, plastic or ceramic and decorative forms comprising a variety of colors, glow-in-the-dark and LED lights which may be activated by the patient tapping their teeth together.*

*58. The rotating clip orthodontic bracket comprising:*

*an orthodontic bracket comprising a body, the body having a back, a front with a center, left and right sides, a top and a bottom, the body front contains an archwire slot extending horizontally left side to right side shaped to receive an orthodontic archwire with right and left ends, left and right tie wings at the top and bottom body for tie wires or elastomeric ties for securing an archwire within the archwire slot;*

*a cylindrical recess with walls in the center of the body front of the orthodontic bracket wherein the cylindrical recess is open on the bracket body front and extends towards the bracket body back wherein the cylindrical recess ends with a circular floor; and*

*a rotating clip within the cylindrical recess for securing orthodontic archwires comprised of a circular base, two attached opposing columns separated by open opposing sides which allow the passage of an archwire through the archwire slot, the columns supporting first and second opposing sets of c-shaped extensions, the first set with a c-shaped extension adjacent to the top left tie wing, wherein the first opposing c-shaped extension end undersides each have a bump and the second opposing c-shaped extension end undersides are each flat, the circular base is fitted to the cylindrical recess wall adjacent to the circular floor, the opposing columns are fitted to the cylindrical recess walls and the c-shaped extensions extend on the bracket front in opposing directions, the clip is fitted in the cylindrical recess and when the rotating clip is in a center position the bracket slot is open allowing the insertion and removal of an archwire in the archwire slot, when the rotating clip is rotated in a counterclockwise position the bumps, on the underside of the c-shaped extensions, push on the archwire to retain the archwire actively within the archwire slot at the right and left ends of the archwire slot, when the rotating clip is rotated clockwise the flat undersurface of the c-shaped extensions push on the archwire holding hold the archwire passively in the archwire slot.*

*59. The rotating clip orthodontic bracket of claim 58 further comprising top and bottom index pin notches positioned between adjacent tie wings in the center of the front of the bracket body wherein an index pin with a measuring notch is placed to guide the placement of the orthodontic bracket on a tooth.*

*60. The rotating clip orthodontic bracket clip of claim 58 wherein the c-shaped extensions free ends each have a surface facing the front of the body of the orthodontic bracket, this surface is beveled towards the free ends which facilitates sliding the c-shaped extension over an orthodontic archwire that has been placed in the archwire slot.*

*61. The rotating clip orthodontic bracket of claim 58 wherein the bracket face has cutouts adjacent to the archwire slot shaped to receive c-shaped extension ends with underside bumps and a channel on the bracket face with adjacent underside bumps on the c-shaped extensions wherein the cutouts guide the underside bumps during the rotation of the rotating clip.*

*62. The rotating clip orthodontic bracket of claim 58 wherein the c-shaped extensions have a middle which contain an extension tab which projects towards the archwire slot, the extension tab encloses the archwire when the rotating clip is in the closed position thus increasing the closure of the archwire in the archwire slot.*

*63. The rotating clip orthodontic bracket of claim 58 wherein the top left and right wings have horizontal notches extending to the body center from the left of the bracket and the lower right and left wings have horizontal notches extending to the body center from the of the bracket, the notches allow attachment of orthodontic elastomeric power chains to the upper wings only or to the lower wings only.*

*64. The rotating clip orthodontic bracket of claim 58 wherein there are upper and lower index pin notches to receive an index pin with a horizontal measuring notch for positioning the orthodontic bracket upon a tooth.*

*65. The rotating clip orthodontic bracket of claim 58 wherein the cylindrical wall has a circular ring and the attached columns of the rotating clip has a circular groove, when circular ring is seated in the circular groove the rotating clip is allowed to rotate without being unseated from the cylindrical recess.*

*66. The rotating clip orthodontic bracket of claim 58 which is comprised of a variety of materials selected from the group consisting of metal, plastic and ceramic and decorative forms comprising a variety of colors, glow-in-the-dark and LED lights which may be activated by the patient tapping their teeth together.*

*67. A method of straightening teeth using the rotating clip orthodontic bracket of claim 58, comprising:*

*attaching a rotating orthodontic bracket to a tooth;*

*rotating the orthodontic bracket rotating clip to an archwire slot open position;*

*placing an orthodontic archwire into the archwire slot;*

*enclosing the archwire by rotating the rotating clip until the archwire is enclosed within the archwire slot;*

*opening the orthodontic archwire slot by rotating the rotating clip into an archwire slot is open; and*

*removing the orthodontic archwire.*

* * * * *